(12) United States Patent
Battles

(10) Patent No.: US 8,414,486 B2
(45) Date of Patent: Apr. 9, 2013

(54) PORTAL APPARATUS WITH A FINGER SEAL ASSEMBLY

(75) Inventor: Christopher Battles, Seymour, CT (US)

(73) Assignee: Covidien LP, Mansfield, MA (US)

( * ) Notice: Subject to any disclaimer, the term of this patent is extended or adjusted under 35 U.S.C. 154(b) by 90 days.

(21) Appl. No.: 13/021,031

(22) Filed: Feb. 4, 2011

(65) Prior Publication Data

US 2011/0237899 A1    Sep. 29, 2011

Related U.S. Application Data

(60) Provisional application No. 61/317,304, filed on Mar. 25, 2010.

(51) Int. Cl.
*A61B 1/32* (2006.01)
(52) U.S. Cl. .................................................. 600/208
(58) Field of Classification Search ........... 600/201–227
See application file for complete search history.

(56) References Cited

U.S. PATENT DOCUMENTS

| | | | |
|---|---|---|---|
| 3,007,527 | A | 11/1961 | Nelson |
| 4,610,665 | A * | 9/1986 | Matsumoto et al. ..... 604/167.04 |
| 4,762,125 | A | 8/1988 | Leiman et al. |
| 5,376,077 | A | 12/1994 | Gomringer |
| 5,385,552 | A | 1/1995 | Haber et al. |
| 5,743,884 | A * | 4/1998 | Hasson et al. ........... 604/167.02 |
| 2005/0171479 | A1 | 8/2005 | Hruska et al. |
| 2010/0234688 | A1* | 9/2010 | Carter ........................... 600/208 |
| 2012/0108905 | A1* | 5/2012 | Carter et al. .................. 600/208 |

FOREIGN PATENT DOCUMENTS

| | | |
|---|---|---|
| WO | WO2008/085772 | 7/2008 |
| WO | WO2008/093313 | 8/2008 |

OTHER PUBLICATIONS

S. Kitano, et al., "A New Sealing Device (Sandwich-disc) For Rapid Recreation of Pneumoperitoneum During Laparoscopic Assisted Surgery", Surgical Endoscopy (1996) vol. 10, 1031-1032, Springer Verlag, New York 1996.
European Search Report for EP 10 25 0548 date of completion is Jun. 25, 2010 (3 pages).

* cited by examiner

*Primary Examiner* — Eduardo C Robert
*Assistant Examiner* — James Palmer

(57) ABSTRACT

A surgical portal assembly includes a portal member defining a longitudinal axis and having a longitudinal passageway for passage of a surgical object, and being dimensioned to pass through tissue to provide access via the longitudinal passageway to an underlying operative site and a plurality of object seals in mechanical cooperation with the portal member and positioned to intersect the longitudinal passageway. Each object seal has inner surfaces defining a seal passage to permit passage of the surgical object. The inner seal surfaces of each object seal include a primary finger segment and secondary finger segments on opposed sides of, and in spaced relation to, the primary finger segments. The primary finger segment and the secondary finger segments depend inwardly relative to the seal passage with adjacent object seals being angularly displaced relative to each other through an arc of rotation about the longitudinal axis whereby the primary finger segments and the secondary finger segments of respective object seals at least partially overlap and cooperate to establish a substantial sealed relation with the surgical object. The object seals may each include a tertiary finger segment on opposed sides of, and in spaced relation to, the secondary finger segments.

20 Claims, 3 Drawing Sheets

PORTAL APPARATUS WITH A FINGER SEAL ASSEMBLY

CROSS REFERENCE TO RELATED APPLICATION

The present application claims the benefit of and priority to U.S. Provisional Application Ser. No. 61/317,304 filed on Mar. 25, 2010, the entire contents of which are incorporated herein by reference.

BACKGROUND

1. Technical Field

The present disclosure relates to a portal apparatus adapted to allow the introduction of surgical instrumentation into a patient's body. In particular, the present disclosure is directed to a portal apparatus including a seal assembly adapted to establish a substantial sealed relation with a surgical object.

2. Description of the Related Art

In laparoscopic procedures, surgery is performed in the interior of the abdomen through a small incision; in endoscopic procedures, surgery is performed in any hollow viscous of the body through narrow tubes or cannula inserted through a small entrance incision in the skin. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. Moreover, laparoscopic and endoscopic procedures often require the surgeon to treat organs, tissues, and vessels far removed from the incision, thereby requiring that any instruments used in such procedures be relatively long and narrow. Generally in the context of insufflatory surgical procedures, a substantially fluid-tight seal about an instrument being introduced within the portal is desirable.

SUMMARY

Accordingly, the present disclosure is directed to a surgical portal assembly including a portal member defining a longitudinal axis and having a longitudinal passageway for passage of a surgical object, and at least one object seal in mechanical cooperation with the portal member and positioned to intersect the longitudinal passageway. The portal member is dimensioned to pass through tissue to provide access via the longitudinal passageway to an underlying operative site. The at least one object seal has inner surfaces defining a seal passage to permit passage of the of the surgical object. The inner seal surfaces include at least two fingers depending inwardly relative to the seal passage and being spaced relative to each other, and cooperating to establish a substantial sealed relation with the surgical object.

First and second object seals may be incorporated and arranged in superposed relation. The second object seal may be angularly displaced relative to the first object seal through an arc of rotation about the longitudinal axis whereby the at least two fingers of the first and second object seals overlap. A third object seal may be arranged in superposed relation with the first and second object seals. The third object seal is rotatably displaced relative to the second object seal through an arc of rotation about the longitudinal axis whereby the at least two fingers of the second and third object seals overlap. A fourth object seal is also contemplated.

The inner surfaces of each of the first and second seals may include three fingers depending inwardly relative to the seal passage whereby adjacent fingers of each of the first and second seals are in spaced relation.

In another embodiment, a surgical portal assembly includes a portal member defining a longitudinal axis and having a longitudinal passageway for passage of a surgical object, and being dimensioned to pass through tissue to provide access via the longitudinal passageway to an underlying operative site, and a plurality of object seals in mechanical cooperation with the portal member and positioned to intersect the longitudinal passageway. Each object seal has inner surfaces defining a seal passage to permit passage of the surgical object. The inner seal surfaces of each object seal include a primary finger segment and secondary finger segments on opposed sides of, and in spaced relation to, the primary finger segments. The primary finger segment and the secondary finger segment depend inwardly relative to the seal passage. Adjacent object seals are angularly displaced relative to each other through an arc of rotation about the longitudinal axis whereby the primary finger segments and the secondary finger segments of respective object seals at least partially overlap and cooperate to establish a substantial sealed relation with the surgical object. The object seals may each include a tertiary finger segment on opposed sides of, and in spaced relation to, the secondary finger segments.

First, second and third object seals may be incorporated with the first, second and third object seals being angularly displaced through predetermined arcs of rotation about the longitudinal axis. A fourth object seal may also be provided. The second object seal may be angularly displaced relative to the first object seal through a first predetermined arc of rotation about the longitudinal axis, the third object seal may be angularly displaced relative to the second object seal through a second predetermined arc of rotation about the longitudinal axis, and the fourth object seal may be angularly displaced relative to the third object seal through a third predetermined arc of rotation about the longitudinal axis. The first, second and third predetermined arcs of rotation may be substantially equal. The first, second and third predetermined arcs of rotation may be substantially ninety degrees.

The primary finger segments and the secondary finger segments of the object seals may be dimensioned to cooperate to substantially close the longitudinal passageway of the portal member in the absence of the surgical object.

BRIEF DESCRIPTION OF THE DRAWINGS

Various embodiments of the present disclosure are described herein with reference to the drawings wherein.

DETAILED DESCRIPTION

The portal apparatus of the present disclosure contemplates the introduction of various types of instrumentation adapted for insertion through a trocar and/or cannula assembly and incorporates a seal assembly adapted to maintain a substantially fluid-tight interface about the instrument to help preserve the atmospheric integrity of a surgical procedure from gas and/or fluid leakage. This feature of the present disclosure minimizes the entry and exit of gases and/or fluids to/from the body cavity.

Examples of instrumentation include, but are not limited to, clip appliers, graspers, dissectors, retractors, staplers, laser probes, photographic devices, endoscopes and laparoscopes, tubes, and the like. Such instruments will collectively be referred to as "instruments", "instrumentation" or "surgical objects" which also may include the hand of a clinician.

The portal assembly may be any suitable cannula assembly used in laparoscopic or arthroscopic procedures. The portal assembly may also be adapted to receive the hand of a surgeon during, e.g., a minimally invasive laparoscopic hand assisted procedure.

In the following description, as is traditional, the term "proximal" or "trailing" refers to the portion of the device closer to the operator while the term "distal" or "leading" refers to the portion of the device further from the operator.

Figure 1:
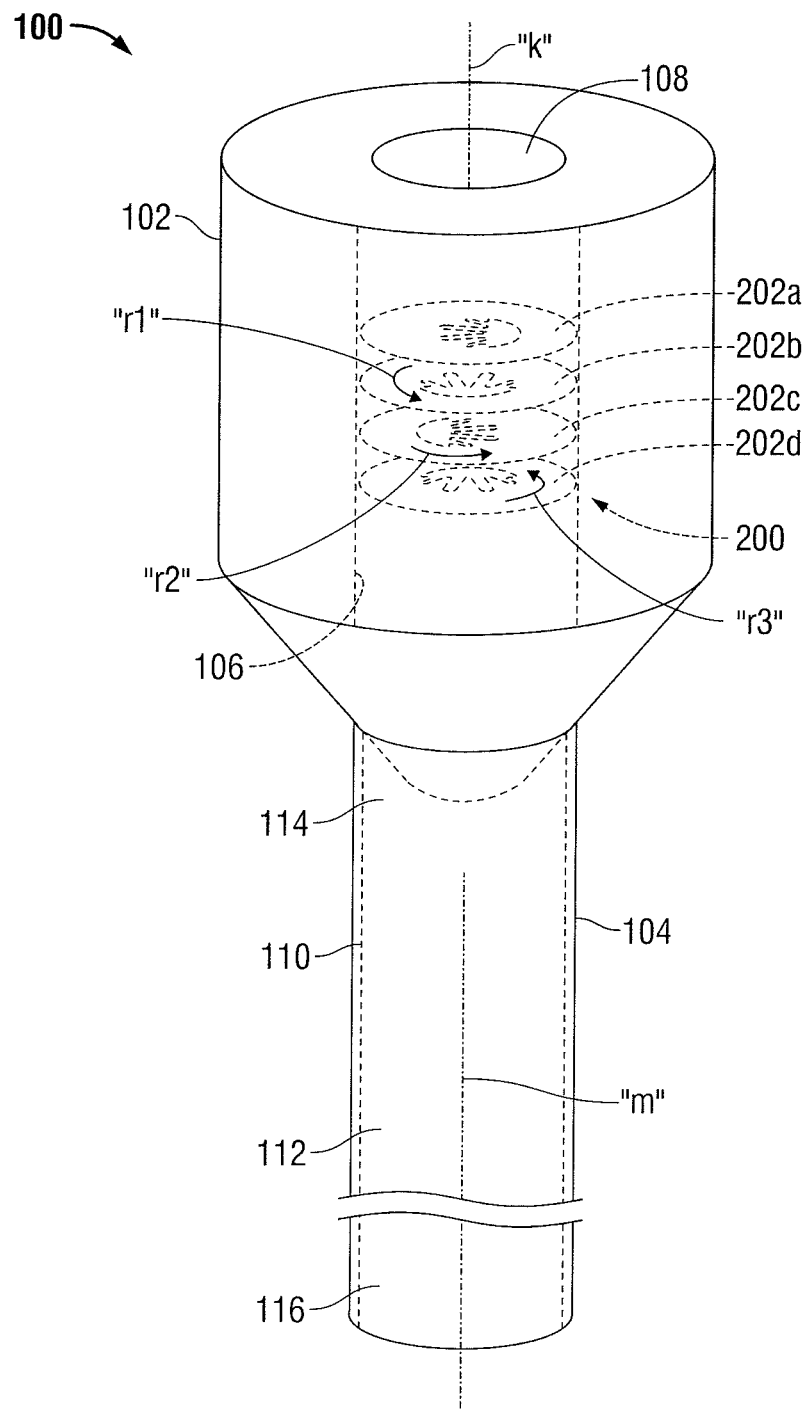
FIG. 1 is a perspective view of a surgical portal apparatus including a seal assembly (in phantom) in accordance with the present disclosure.

Referring now to the drawings, in which like reference numerals identify identical or substantially similar parts throughout the several views, FIG. 1 illustrates an exemplary embodiment of the portal apparatus 100 in accordance with the principles of the present disclosure. Portal apparatus 100 may be a laparoscopic cannula assembly utilized in conjunction with a laparoscopic surgical procedure where the peritoneal cavity is insufflated with a suitable gas, e.g., $CO_2$, to raise the cavity wall from the internal organs therein. The cannula assembly may be used with an obturator assembly (not shown) which is a sharp pointed instrument positionable within the passageway of the cannula assembly. The obturator assembly is utilized to penetrate the abdominal wall and then subsequently removed from the cannula assembly to permit introduction of the surgical instrumentation utilized to perform the procedure. In the alternative, portal apparatus 100 may be an arthroscopic cannula assembly used in connection with an arthroscopic surgical procedure.

Portal apparatus 100 includes portal housing 102 and elongated portal member 104 extending from the portal housing 102. Portal housing 102 may include multiple housing segments connected to each other via convention means or may be a single component integrally or monolithically formed. Portal housing 102 has inner housing wall 106 defining housing passage 108 coaxially arranged about a longitudinal housing axis "k" extending through the portal housing 102. Inner housing wall 106 is dimensioned to receive a surgical object or instrument (not shown) and laterally confine the instrument within portal housing 102. Inner housing wall 106 may be generally circular in cross-section or may assume other cross-sectional shapes.

Portal member 104 may be a sleeve member defining a longitudinal portal axis "m" extending along the length of the portal member 104. Longitudinal portal axis "m" of portal member 104 may be in general longitudinal alignment with longitudinal housing axis "k". Portal member 104 includes outer sleeve wall 110 defining an internal longitudinal opening 112 extending from proximal or trailing end 114 through distal or leading end 116 of the portal member 104. Longitudinal opening 112 of portal member 104 is in general longitudinal alignment with central housing passage 108 of portal housing 102 to define a common longitudinal passageway 108, 112 through portal apparatus 100 for passage of the surgical object. Portal member 102 may be a separate component connected to portal housing 102 or may be monolithically formed with the portal housing 102. Portal member 104 and portal housing 102 may be releasably connected through a variety of mechanisms including, e.g., through a bayonet lock, threaded connection, or the like.

Portal member 104 may be formed of stainless steel or other rigid materials such as a polymeric material or the like. Portal member 104 may be clear or opaque. The diameter of portal member 104 may vary, but typically ranges from about 3 to about 15 mm when used in a laparoscopic or arthroscopic technique. If used in a hand assisted minimally invasive approach, the diameter of portal member may be substantially greater than 15 mm.

Figure 2:
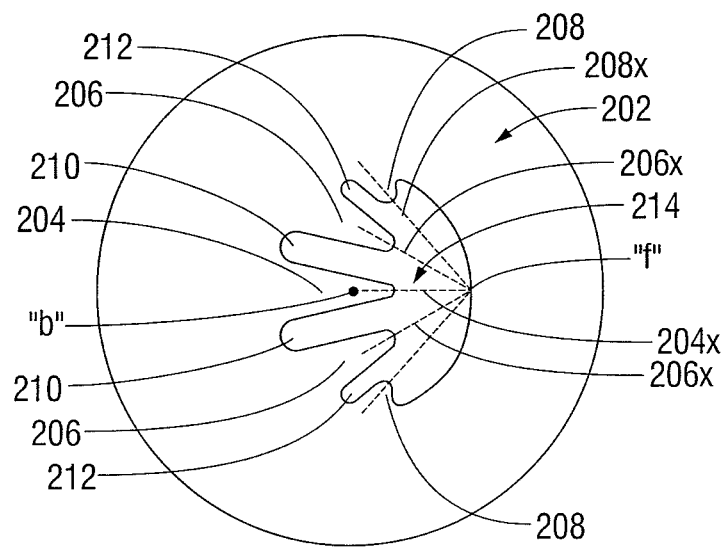
FIG. 2 is a top plan view of one object seal of the seal assembly of FIG. 1 illustrating the primary, secondary and tertiary finger segments of the object seal.
Figure 3:
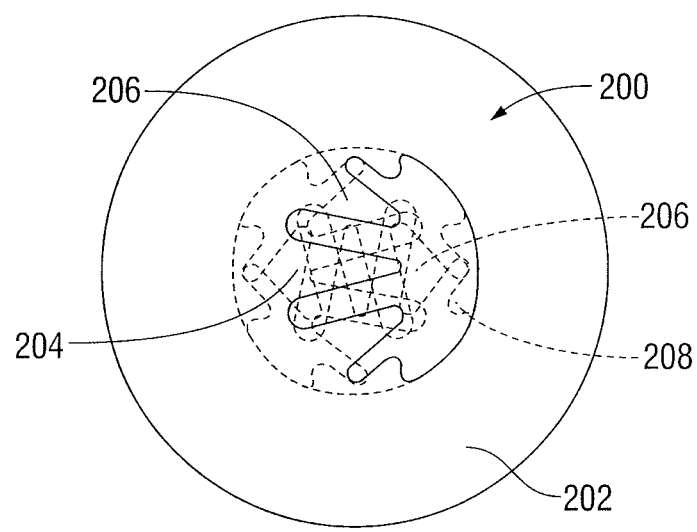
FIG. 3 is a top plan view of the seal assembly of FIG. 1 illustrating the plurality of object seals and respective finger segments in overlapping relation.
Figure 4:
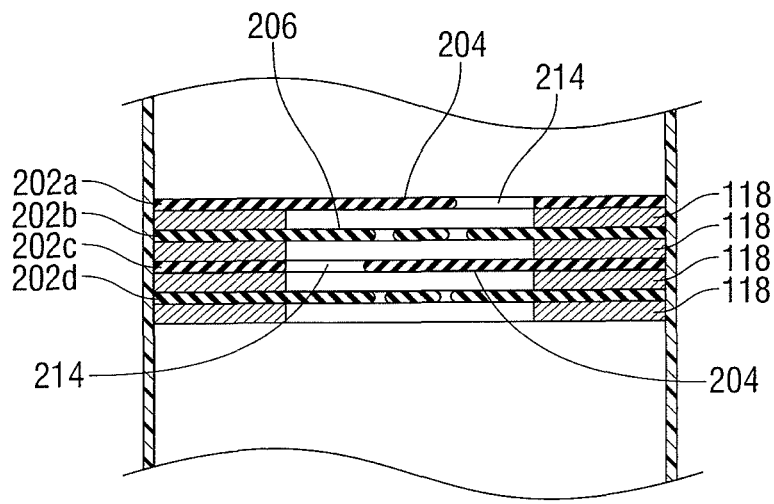
FIG. 4 is a side cross-sectional view illustrating the seal assembly.

Referring now to FIGS. 2-4, in conjunction with FIG. 1, portal apparatus 100 further includes a seal assembly 200 which is mounted within portal housing 102. Seal assembly 200 includes a plurality of object seals 202a-d which function in concert to establish a seal about an inserted surgical object. The plurality of seals 202 may also substantially close housing passage 108 in the absence of a surgical object thereby preventing exit of fluids and preserving the integrity of the underlying pneumoperitoneum. Two, three, four or more object seals 202 may be incorporated within seal assembly 200 and disposed in stacked or superposed relation. Each seal 202 may be substantially identical in structure.

FIG. 2 illustrates one object seal 202 in plan view. Object seal 202 defines central seal axis "b" which extends through the general center of the seal 202. Object seal 202 includes inner surfaces which define central primary finger 204, secondary fingers 206 on opposed sides of central primary finger 204 and tertiary fingers 208 on opposed sides of secondary fingers 206. Secondary fingers 206 are spaced from primary finger 204 through slots 210 and tertiary fingers 208 are spaced from secondary fingers 206 through respective slots 212. Primary finger 204 is slightly greater in length than secondary fingers 206. Tertiary fingers 208 extend for about one-half the length of secondary fingers 206. Other relative lengths for primary, secondary and tertiary fingers 204, 206, 208 are also envisioned. Primary, secondary and tertiary fingers 204, 206, 208 may be symmetrically arranged about respective finger axes 204x, 206x, 208x. Axes 204x, 206x, 208x of primary, secondary and tertiary fingers 204, 206, 208 may extend to meet at a common focal point "f" as depicted in FIG. 2 or may be offset.

The inner surfaces of object seal 202 further define seal passage or aperture 214 towards which primary, secondary and tertiary fingers 204, 206, 208 extend. Seal passage 214 in combination with slots 210, 212 permit passage of the surgical object through seal 202. Seal passage 214 may be general D-shaped in configuration. Seal passage 204 and slots 210, 212 may resemble the hands and/or fingers of a human.

The materials of fabrication of object seal 202 may include a suitable elastomeric material whereby the inner portions, conform to establish the seal about the surgical object. One suitable seal material which may be adapted for incorporated seal 202 is disclosed in commonly assigned U.S. Pat. No. 6,482,181 to Racenet et al., the entire contents of which are hereby incorporated by reference herein. The seal disclosed in the Racenet '181 patent includes an elastomeric material (such as isoprene or natural rubber) and at least one layer of fabric material. The fabric material may be any suitable fabric, for example, A SPANDEX material containing about 20% LYCRA and about 80% NYLON available from Milliken. The elastomeric material may be adhered to or embedded within the fabric material. Object seal 202 may be coated with a hydrophilic coating to facilitate passage of the surgical object.

With reference to FIGS. 1-4, object seals 202a-d are angularly displaced relative to each other through predetermined arcs of rotation. For example, the first (trailing or proximal most) seal 202a may be arranged at one orientation with respect to the longitudinal axis. Adjacent second seal 202b, which is distal of first seal 202a, may be angularly displaced relative to the first object seal 202 through an arc of rotation "r1" about the housing axis "k" (FIG. 1). In this arrangement, at least some of primary, secondary and tertiary fingers 204, 206,208 of first and second seals 202a, 202b overlap. Third seal 202c, which is adjacent to and distal of second seal 202b, may be angularly displaced relative to the second object seal 202b through an arc of rotation "r2" and fourth seal 202d, which is adjacent to and distal of third seal 202c may be angularly displaced relative to the third object seal 202c through an arc of rotation "r3". The arcs of rotations "r1", "r2", "r3" may be the same or different for adjacent seals 202. In one embodiment, the arc of rotation "r1", "r2", "r3" may range from about 10 degrees to about 150 degrees. In an embodiment with four seals constituting seal assembly 200, the arc of rotation "r1", "r2", "r3" may be about 90 degrees. This arrangement is depicted in FIGS. 1, 3 and 4. In this embodiment, primary, secondary and tertiary fingers 204, 206, 208 of the four seals 202 overlap in a manner which may substantially close central housing passage 108 in the absence of the surgical object thereby preventing escape of gases and maintaining the integrity of the established pneumoperitoneum.

Object seals 202a-202d may be mounted within portal housing 102 by conventional means such as with the use of adhesives, cements, spot welding or the like. In one embodiment best depicted in FIG. 4, portal housing 102 includes a plurality or spaced annular mounting elements 118 which are secured or integrally formed within portal housing 102. Object seals 202a-202d may be secured adjacent their peripheral areas to mounting elements 118 with the use of cements or adhesives. Second, third and fourth object seals 202b, 202c 202d may be retained within adjacent mounting elements 118 and possibly secured relative to the mounting elements 118 via friction fit and/or adhesives. The spacing of annular mounting elements 118 correspondingly arranges objects seals 202-202d in spaced relation with respect to the housing axis "k". This permits adequate flexing of primary, secondary and tertiary fingers 204, 206, 208 of object seals 202a-202d during passage of the surgical object.

In one embodiment, portal housing 102 may also include a zero closure valve 120 disposed in mechanical cooperation within housing 102 (FIG. 1). Zero closure valve 120 may be, e.g., a duckbill valve, slit valve, trumpet valve or the like adapted to provide a substantially fluid-tight seal in absence of a surgical object.

Figure 5:
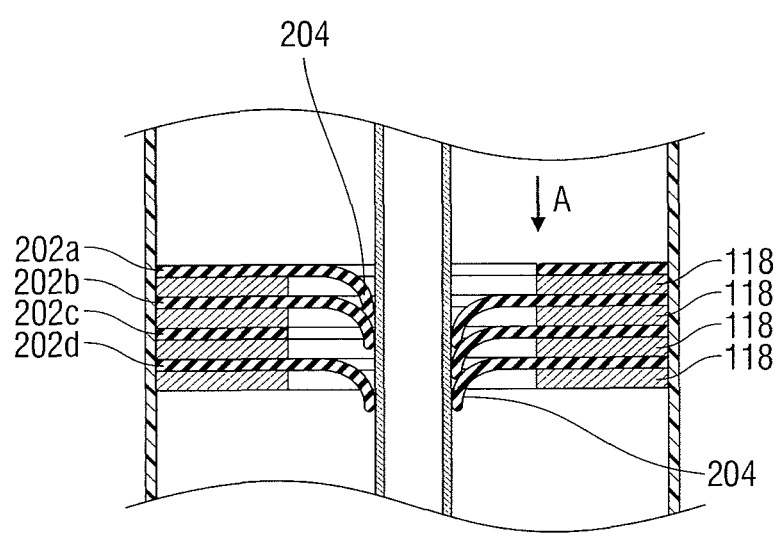
FIG. 5 is a side cross-sectional view similar to the view of FIG. 4 illustrating introduction of a surgical object through the seal assembly.

During use, a surgical object or surgical instrument "I" (shown in FIG. 5) is introduced through the housing passage 108 and through seal passages 214 of seals 202a-202d. The surgical instrument "I" is advanced through seal assembly 200 and longitudinal opening 108 of portal member 102 whereby primary, secondary and tertiary fingers 204,206,206 cooperate to establish a seal about the surgical instrument "I". Upon withdrawal of the surgical instrument "I", primary, secondary and tertiary fingers 204,206,206 of seals 202a-202d cooperate to close housing passage 108 (FIG. 4).

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical portal assembly, which comprises:
   a portal member defining a longitudinal axis and having a longitudinal passageway for passage of a surgical object, the portal member dimensioned to pass through tissue to provide access via the longitudinal passageway to an underlying operative site; and
   at least one object seal in mechanical cooperation with the portal member and positioned to intersect the longitudinal passageway, the at least one object seal having inner surfaces defining a seal passage to permit passage of the of the surgical object, the inner seal surfaces including at least two fingers depending inwardly relative to the seal passage and being spaced relative to each other, and cooperating to establish a substantial sealed relation with the surgical object, the at least two fingers having different lengths and defining a slot therebetween, the slot in communication with the seal passage.

2. The surgical portal assembly according to claim 1 including first and second object seals in superposed relation, the second object seal being angularly displaced relative to the first object seal through an arc of rotation about the longitudinal axis whereby the at least two fingers of the first and second object seals overlap.

3. The surgical portal assembly according to claim 2 further including a third object seal arranged in superposed relation with the first and second object seals, the third object seal being rotatably displaced relative to the second object seal through an arc of rotation about the longitudinal axis whereby the at least two fingers of the second and third object seals overlap.

4. The surgical portal assembly according to claim 2 wherein the inner surfaces of each of the first and second seals include three fingers depending inwardly relative to the seal passage, adjacent fingers of each of the first and second seals being in spaced relation.

5. The surgical portal assembly according to claim 4 including a third object seal in superposed relation with the first and second object seals, the first, second and third object seals being angularly displaced through predetermined arcs of rotation about the longitudinal axis.

6. The surgical portal assembly according to claim 5 including a fourth object seal.

7. The surgical portal assembly according to claim 2 wherein the inner surface of each of the first and second seals include three fingers depending inwardly relative to the seal passage.

8. The surgical portal assembly according to claim 7 wherein the inner surfaces define an arcuate aperture toward which the first and second fingers extend.

9. The surgical portal assembly according to claim 8 wherein each of the first and second object seals include first, second and third fingers, adjacent fingers being in spaced relation.

10. A surgical portal assembly, which comprises:
    a portal member defining a longitudinal axis and having a longitudinal passageway for passage of a surgical object, the portal member dimensioned to pass through tissue to provide access via the longitudinal passageway to an underlying operative site; and
    a plurality of object seals in mechanical cooperation with the portal member and positioned to intersect the longitudinal passageway, each object seal having inner surfaces defining a seal passage to permit passage of the surgical object, the inner seal surfaces of each object seal including a primary finger segment and secondary finger segments on opposed sides of, and in spaced relation to, the primary finger segments, the primary finger segment and the secondary finger segments depending inwardly relative to the seal passage, adjacent object seals being angularly displaced relative to each other through an arc of rotation about the longitudinal axis whereby the primary finger segments and the secondary finger segments of respective object seals at least partially overlap and cooperate to establish a substantial sealed relation with the surgical object, the primary finger segment and the secondary finger segments of each object seal extending towards a common focal point offset from the center of the respective object seal.

11. The surgical portal assembly according to claim 10 wherein the object seals each include a tertiary finger segment on opposed sides of, and in spaced relation to, the secondary finger segments.

12. The surgical portal assembly according to claim 10 including first, second and third object seals, the first, second and third object seals being angularly displaced through predetermined arcs of rotation about the longitudinal axis.

13. The surgical portal assembly according to claim 12 including a fourth object seal.

14. The surgical portal assembly according to claim 13 wherein the second object seal is angularly displaced relative to the first object seal through a first predetermined arc of rotation about the longitudinal axis, the third object seal is angularly displaced relative to the second object seal through a second predetermined arc of rotation about the longitudinal axis, and the fourth object seal is angularly displaced relative to the third object seal through a third predetermined arc of rotation about the longitudinal axis.

15. The surgical portal assembly according to claim 14 wherein the first, second and third predetermined arcs of rotation are substantially equal.

16. The surgical portal assembly according to claim 15 wherein the first, second and third predetermined arcs of rotation are substantially ninety degrees.

17. The surgical portal assembly according to claim 10 wherein the primary finger segments and the secondary finger segments of the object seals are dimensioned to cooperate to substantially close the longitudinal passageway of the portal member in the absence of the surgical object.

18. The surgical portal assembly according to claim 10, wherein the secondary finger segments of each object seal are symmetrically arranged with respect to the primary finger segment.

19. The surgical portal assembly according to claim 10, wherein the primary finger segment and the secondary finger segments of each object seal have different lengths.

20. The surgical portal assembly according to claim 19, wherein the seal passage of each object seal defines an opening in the absence of the surgical object therethrough.

* * * * *